United States Patent [19]

Nerbe et al.

[11] Patent Number: 5,013,590
[45] Date of Patent: May 7, 1991

[54] BIOCHEMICAL REACTION RECEPTACLE

[76] Inventors: Jürgen F. Nerbe, Ansgarstrasse 8, D-2105 Seevetal 11; Karl-Georg Wönne, Zum dicken Busch 12b, D-2000 Barsüttel, both of Fed. Rep. of Germany

[21] Appl. No.: 243,037

[22] PCT Filed: Oct. 31, 1987

[86] PCT No.: PCT/EP87/00649
§ 371 Date: Jun. 23, 1988
§ 102(e) Date: Jun. 23, 1988

[87] PCT Pub. No.: WO88/03648
PCT Pub. Date: May 19, 1988

[30] Foreign Application Priority Data

Nov. 3, 1986 [DE] Fed. Rep. of Germany ....... 3637421

[51] Int. Cl.$^5$ ........................ G01N 33/545; B01L 3/00
[52] U.S. Cl. ................................... 428/36.4; 422/102; 428/36.92
[58] Field of Search .............. 422/102; 428/364, 36.92

[56] References Cited

FOREIGN PATENT DOCUMENTS

| 592771 | 3/1990 | Australia . |
| 0097573 | 1/1984 | European Pat. Off. . |
| 0126392 | 11/1984 | European Pat. Off. . |
| 0164889 | 12/1985 | European Pat. Off. . |
| 0175195 | 3/1986 | European Pat. Off. . |
| 2545749 | 5/1976 | Fed. Rep. of Germany . |
| 2332287 | 6/1977 | France . |
| 1571182 | 7/1980 | United Kingdom . |

OTHER PUBLICATIONS

Chemical Abstracts, *Textiles*, vol. 79, p. 71, 1973.

*Primary Examiner*—James J. Seidleck
*Attorney, Agent, or Firm*—Walter C. Farley

[57] ABSTRACT

A reaction receptacle made of a chemically inert thermoplastic and used in carrying out reactions with biospecific compounds, preferably for medical lab diagnosis, is characterized by adding a non-migratory substance to the plastic prior to its thermoplastic shaping in such a manner that following said shaping, molecules with reactive groups of atoms of the incorporated substance shall be exposed at least at the receptacle inside surface.

9 Claims, No Drawings

BIOCHEMICAL REACTION RECEPTACLE

The invention relates to a reaction vessel made of a chemically inert thermoplastic with a substance incorporated therein, the substance having molecules at the surface of the receptacle with reactive groups of atoms.

BACKGROUND OF THE INVENTION

Reaction receptacles are used in biological laboratories or in biochemical processing and especially in clinical laboratory diagnosis. They serve to carry out biochemical reactions of the most diverse kinds, employing chemical reactions with biospecific compounds where at least one of the reagents is a protein, namely a protein molecule or a fragment of it. Such analysis is carried out large-scale on blood samples, for instances to test patients for pathological symptoms or to analyze donor blood in blood banks. The chemical reactions that are carried out are most diverse in nature, and thus they include enzyme reactions, hormone reactions, antigenantibody reactions or blood-coagulating reactions, the last usually taking place at the beginning of a blood test.

Such reaction receptacles are used today in large numbers at low prices so as to be economically justifiable for instance in clinical large-scale labs of conventional size.

Accordingly the material used for these reaction receptacles has been a thermoplastic which allows making economical reaction receptacles and which, on account of its chemical inertness, does not affect the reactions taking place in the receptacle.

In the state of the art, the reagent required for the biochemical reaction must be added to the test material in such reaction receptacles. This entails a disadvantageous additional operational step. Moreover another drawback must frequently be incurred, namely that the added reagent must be separated again before the next test is carried out since otherwise there will be interference and, again, additional operational steps must be carried out.

SUMMARY OF THE INVENTION

Accordingly it is the object of the present invention to create a reaction receptacle wherein biochemical reactions can be carried out in less time and with less labor.

Briefly described, the invention includes a reaction receptacle made of a chemically inert thermoplastic to carry out chemical reactions with biospecific compounds, preferably for use in medical laboratory diagnosis. The plastic is so treated by the addition of a non-migrating incorporated substance prior to its thermoplastic shaping that, following this shaping, molecules with reactive groups of atoms of the incorporated substance are present at least at the inside surface of the receptacle.

In the invention, a substance is added to the plastic of the reaction receptacle so it will be incorporated into this plastic, when this plastic melts but before the plastic is thermoplastically shaped so that the substance be non-migrating. "Non-migrating" means with respect to the present technology that the added substance shall be so bound to the plastic that it will not be transferred, not even in slight amounts, to the test sample. The added substance comprises molecules with chemically reactive groups of atoms. The incorporation into the plastic is carried out in such a way that at least a substantial number of the reactive groups of atoms of the added molecule of said substance shall be located and exposed at the bare surface of the plastic. Accordingly, the reaction receptacle of the invention evinces reactive groups of atoms on at least its inside surface which come in contact with the filled test sample, where these reactive groups of atoms can be directly used for the desired reaction without separating from the plastic, or else allow binding a desired ligand which, together with the test sample, will result in the desired reaction. The significant advantage obtained thereby is that the molecule of the substance bearing the reactive groups of atoms or the ligands bound to that molecule are available for the reaction but do not enter the test sample.

After the reaction has been carried out, the test sample can be removed without being contaminated by the molecule of the incorporated substance or by the ligands bound to that molecule. This eliminates subsequent separation steps. Obviously, addition of the reagent also is eliminated because this reagent for the test sample now already is bound to the receptacle wall. Thereby biochemical analysis is substantially simplified and accelerated. It is a further great advantage to achieve the versatility provided by the invention on account of such free groups of atoms or ligands bound to them, which take part only catalytically in the reaction, that is, without being used up. Especially regarding medical lab diagnosis in mass testing, for instance of blood samples, several samples can be made to react sequentially in one reaction receptacle of the invention with no more being required than merely rinsing between samples. In clinical large-scale analysis, for instance in blood banks, substantial savings will be possible thereby, which represents a large factor in today's cost-control endeavors.

Further advantages are provided by providing reactive groups which are hydrophilic. Blood serum obtained from whole blood by a blood coagulation reaction is required to test the patient's blood for pathological symptoms. That reaction can be constrained by chemical substances, yet this approach would be a drawback for the subsequent serum analyses. Therefore the naturally-occurring blood coagulation reaction is preferred, which is initiated by mechanical lesion of the thrombocytes with ensuing release of prothrombin as the initiating enzyme of the coagulation chain. A reaction receptacle of the initially cited kind and operating on this principle is known from the German Offenlegungsschrift 25 45 749. Sharp-edged particles are added to this known reaction receptacle to cause lesions in the thrombocytes. However those particles thereafter must be removed. In other words, addition and separation steps are required. In the invention, the thrombocyte lesions are caused by hydrophilic reactive groups of atoms at the receptacle wall allowing contact between the thrombocytes and the receptacle wall, where this contact otherwise takes place only exceedingly slowly because of the hydrophobic thermoplastic. In this manner, in a simple way, without any addition to the reaction receptacle, the blood coagulation reaction will be initiated and can very quickly run to completion.

When the added substance is a glycol, this provides advantages. In accordance with the invention, the glycols comprise OH groups as the reactive groups of atoms, which act hydrophilically, that is, they are suitable for the blood coagulation reaction and on the other hand are also suitable to bind desired reagents, illustratively enzymes or proteins. The binding of glycols into plastics of the initially cited kind is problem-free. Ethane diol and propane triol were found especially well suited in experiments.

As shown by pertinent experiments, glycerin glycol is preferred because of its marked hydrophilic action and because it is easily controlled.

Other advantages are provided by adding less than 1% of glycerin glycol. The stated proportion by weight of glycerin glycol, preferably 0.9%, was found optimal in experiments. Deviations by an order of magnitude up or down from this proportion by weight degrade the results only weakly.

A chemically inert powder with hard, sharp-edged particles as added to produce a reaction receptacle to carry out the blood coagulation reaction. Thereby sharp-edged bodies are integrated into the surface of the reaction vessel to increase the lesion-inducing effects in the manner of sandpaper. Thereby the coagulation time may be shortened further by a factor of 10.

Silicate dust may be provided in very fine particles, in the angstrom range, i.e., with very high surface-to-volume ratios. The addition of this very fine material which would otherwise interfere with the liquid is, however, bound into the plastic surface and does not freely move into the serum.

About 1% of silicate dust by weight was found adequate and is so low that the desired physical properties of the plastic remain unaffected. Blood coagulation times of the order of 1 minute can be achieved.

As already mentioned initially, the reactive groups of atoms bared in the plastic surface are directly available for a biochemical reaction, for instance in the manner already cited as hydrophilic groups, to initiate the blood coagulation reaction. However the invention offers the substantive advantage of binding active ligands to the reactive groups of atoms directly or through spacers; in the light of the high processing temperatures when the plastic is thermally shaped, that step must take place subsequently. Such reaction receptacles are applicable on a scope which is almost limitless. Illustratively only a very few examples are given:

The ligands bound to the reactive groups of atoms illustratively are enzymes, antibodies, antigens, hormones or other biospecific molecules. However, substantial fragments of biospecifically active substances also may be bound to the groups of atoms, for instance cell fragments or also other living cells. As a result, while retaining the advantages of the invention, illustratively antigen-antibody reactions may be carried out in fully novel ways.

First a preferred illustrative embodiment mode of a reaction receptacle for carrying out a blood coagulation reaction will be described below.

The reaction receptacle may consist of a suitable thermoplastic. Most applicable are polystyrene, polypropylene, polyethylene, polycarbonate or polyacryl. In particular polystyrene or polypropylene were found especially suitable, which can be employed depending on the manufacturing procedure or the desired mechanical-physical properties of the receptacle in preferred and selective manner. In the preferred embodiment, the two last-mentioned plastics are employed selectively.

As a rule the reaction receptacle will be cylindrical and advantageously already can be used as the syringe barrel when drawing blood from the patient. The blood coagulation reaction takes place in this barrel. Advantageously the receptacle geometry is such that subsequently it can be used in the centrifuge and, where called for thereupon as the primary sample vessel in the analyzing machine, so that refilling and similar steps are eliminated.

In a preferred embodiment the reaction receptacle is manufactured as follows:

225 g. of glycerin glycol and 25 g. of particulate silicate are added to 25 kg of commercial polystyrene or polypropylene granulate. The material is mixed as thoroughly as possible and then is heated to be plasticized and extruded into suitable shapes. Following cooling and ejection from the molds, the reaction receptacles are ready. It is found that the glycol molecules are so solidly anchored into the plastic that none can migrate. The glycol molecules are so imbedded on the plastic surfaces that with fixed, escape-proof incorporation of the molecule residues, OH groups are exposed on the surface where they are then present as the reactive groups of atoms in the sense of the invention.

The blood serum is prepared as follows:

Whole blood is placed in the reaction receptacle described above and, can be so placed as the sample is taken if the receptacle is a syringe barrel. The thrombocytes in the blood make tight contact with the receptacle surface on account of the hydrophilic effect of the bare OH groups of the glycols bound into the plastic, and this contact is especially marked at the tips of the imbedded silicate dust. Thereby the thrombocytes suffer lesions and release the initiator enzyme prothrombin. Henceforth the coagulation sequence takes place.

A waiting time of about 1 minute is required for the described reaction receptacle following the first contact between blood and receptacle. Thus the coagulation reaction already is at an end immediately after and possibly already during the taking of the blood sample. It can be centrifuged at once, with the coagulated solids and the cells being deposited. Thereupon the serum is decanted.

The above embodiment of the reaction receptacle describes adding glycerin glycol and silicate dust to the plastic granulate before plasticizing takes place. Alternatively this material also may be employed premixed as a granulate and illustratively it may be produced in this form directly by the manufacturer.

The described reaction receptacle is characterized by especially good waste-removal (i.e., disposal) properties. These waste-removal properties are unaffected by the thermoplastics used. As an example, harmless combustion is feasible.

Reaction receptacles for further applications within the scope of this invention are manufactured accordingly. In particularly advantageous manner, proteins acting as reagents on the test sample in more complex reactions are bound to the receptacle wall, namely to bare reactive groups of atoms of the incorporated substance. Enzymes may be bound where enzyme reactions will take place. Even living cells can be bound in this manner to the plastic surface and are available in the full scope of their biochemical activities.

The binding of the bio-specifically acting ligands to the bare active groups of atoms of the substance added to the plastic and present in the plastic wall may take place in direct manner or through the known methods of spacers if so required for the particular reaction.

Especially the initially cited glycols can be used as the substance added to the plastic and with bare, reactive groups of atoms, the free OH groups and these glycols being suitable for many binding purposes.

The binding of enzymes is described in illustrative manner below:

First the free OH groups of the glycols bound to the plastic are activated by bromine cyanide (BrCN). These OH groups react with bromine cyanide while forming reactive imido carbon residues. These electrophilic groups bind in a covalent manner with nucleophilic groups of the enzyme which should be immobilized.

The enzyme to be immobilized is introduced in a buffered solution of which the pH is set to the optimal pH of the enzyme. Fixation takes place readily during an incubation time with an optimal duration and temperature that may vary with different enzymes. Any unfixated, excess enzyme is rinsed with the buffer solution.

The amount of the bound enzyme is determined by the difference measurements of enzyme activity in the enzyme solution before and after the binding process, care being taken to account for the residual activities in the rinsing buffer.

Preservation of the enzymes fixed in this manner to the plastic advantageously can be carried out by lyophilization (freeze drying). Such preservation is required if the reaction receptacle now ready for reaction is not used at once. To store the readied reaction receptacle with lyophilized enzymes until it will be used, advantageously the reactive receptacle surface shall be kept in vacuum. Conventional vacuum storage techniques may be used.

Antibodies, hormones or for instance the initially cited living cells may be bound in substantially similar manner. The ligands to be fixed may be treated with radio-isotopes or enzymes if they are to be used subsequently for radio-immuno assay or enzyme-immuno assay.

The described embodiment modes of the reaction receptacles of the invention apply in particular to medical lab diagnosis (for instance to the blood coagulation reaction). Other applications are in biological lab diagnosis of the most diverse purposes. However application to bio-engineering processes also are highly advantageous. Illustratively these latter applications are to the preparation of medicines and foodstuffs, and further to biological waste management. Living cells acting as ligands are especially advantageous in such methods.

We claim:

1. A reaction receptacle for carrying out chemical reactions with biospecific compounds, the receptacle comprising:
    a thermoplastic material shaped to form a body with inner and outer surfaces, and
    a non-migrating incorporated substance having molecules with reactive groups of atoms,
    said thermoplastic material being physically mixed with said non-migrating incorporated substance prior to the shaping of said body and having, after shaping of the body, said molecules of said incorporated substance with reactive groups of atoms exposed at least on the inside surface of the body,
    said thermoplastic material being chemically inert with respect to said incorporated substance and the compounds to be reacted in said receptacle.

2. Reaction receptacle defined in claim 1, characterized in that the reactive groups are hydrophilic.

3. Reaction receptacle according to claim 1, wherein the added substance is a glycol.

4. Reaction receptacle according to claim 2, wherein the added substance is glycerin glycol.

5. Reaction receptacle according to claim 4, wherein the proportion by weight of the glycerin is somewhat less than 1%.

6. Reaction receptacle according to claim 2, and further including a small amount of chemically inert, sharp-edged, hard powder added to the plastic before thermoplastic shaping in addition to said molecules with reactive groups of atoms.

7. Reaction receptacle according to claim 6, characterized in that silicate dust is added.

8. Reaction receptacle according to claim 7, characterized in that the proportion by weight of silicate dust is about 1%.

9. Reaction receptacle according to claim 1 wherein, following the shaping of the reaction receptacle, the reactive groups of atoms bear covalently bound biospecifically active ligands.

* * * * *